(12) United States Patent
Hansson

(10) Patent No.: US 8,922,381 B2
(45) Date of Patent: Dec. 30, 2014

(54) DEVICE AND SYSTEM FOR GAS LEAKAGE DETECTION AND ALARM

(75) Inventor: Bo Hansson, Mersch (LU)

(73) Assignee: LogiCO2 Online SARL, Mersch (LU)

( * ) Notice: Subject to any disclaimer, the term of this patent is extended or adjusted under 35 U.S.C. 154(b) by 0 days.

(21) Appl. No.: 14/233,317

(22) PCT Filed: Jul. 6, 2012

(86) PCT No.: PCT/SE2012/050811
§ 371 (c)(1),
(2), (4) Date: Jan. 16, 2014

(87) PCT Pub. No.: WO2013/012382
PCT Pub. Date: Jan. 24, 2013

(65) Prior Publication Data
US 2014/0132416 A1 May 15, 2014

(30) Foreign Application Priority Data
Jul. 20, 2011 (SE) ...................................... 1150715

(51) Int. Cl.
*G08B 17/10* (2006.01)
*G01N 33/18* (2006.01)
*G01N 21/61* (2006.01)
*G08B 21/14* (2006.01)

(52) U.S. Cl.
CPC ............ *G08B 21/14* (2013.01); *G01N 33/1826* (2013.01); *G01N 21/61* (2013.01); *G01N 33/18* (2013.01)

USPC .......................................... 340/632; 340/603

(58) Field of Classification Search
CPC combination set(s) only.
See application file for complete search history.

(56) References Cited

U.S. PATENT DOCUMENTS

| | | | |
|---|---|---|---|
| 5,053,754 A | 10/1991 | Wong | |
| 5,553,006 A | 9/1996 | Benda | |
| 6,160,487 A * | 12/2000 | DeLuca | 340/693.7 |
| 2006/0170537 A1 | 8/2006 | Marriott | |
| 2007/0063858 A1 | 3/2007 | Lee et al. | |
| 2009/0254315 A1* | 10/2009 | Golinveaux | 703/1 |
| 2010/0117840 A1 | 5/2010 | Rutter et al. | |
| 2011/0068940 A1* | 3/2011 | Kim et al. | 340/632 |

FOREIGN PATENT DOCUMENTS

| | | |
|---|---|---|
| GB | 2358245 A | 7/2001 |
| GB | 2392721 A | 3/2004 |

OTHER PUBLICATIONS

International Search Report and Written Opinion regarding International Application No. PCT/SE2012/050811, mail date Nov. 15, 2012, 10 pages.

\* cited by examiner

*Primary Examiner* — Travis Hunnings
(74) *Attorney, Agent, or Firm* — Foley & Lardner LLP

(57) ABSTRACT

The present invention relates to a gas-detecting unit for detection of $CO_2$ and an alarming unit, said gas-detecting unit and said alarming unit being integrated to comprise one device, and wherein said device is adapted to withstand harsh environments and cleaning of the device.

38 Claims, 2 Drawing Sheets

DEVICE AND SYSTEM FOR GAS LEAKAGE DETECTION AND ALARM

TECHNICAL FIELD

Figures 1, 2:
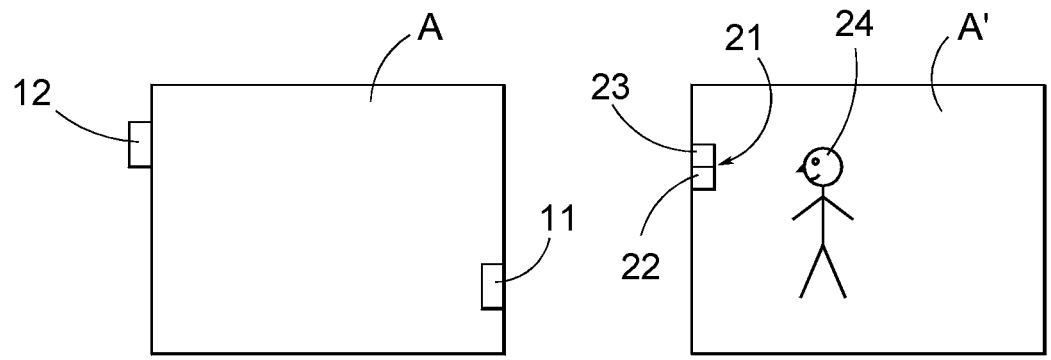

The present invention relates to a device adapted to detect and warn of the presence of $CO_2$.

PRIOR ART $CO_2$ alarm systems of the prior art are produced in compliance with German law, with a pre-alarm and a main alarm, where the pre-alarm issues a warning at 1.5% Short Time Exposure Limit (STEL), and the main alarm issues a warning at 3% STEL. This type of life-saving alarm warns that it is not advisable, or even fatal, for a person to enter the room.

Normally, a sensor is placed in the room where $CO_2$ may occur, such as in a beer cellar, and a central unit is placed outside the room. The central unit warns of the presence of $CO_2$ in the room so that a person may know whether or not the premises can be entered without the risk of exposure to $CO_2$.

Because $CO_2$ is heavier than the normal mixture of gases in the air, the alarm is placed in a non ventilated closed room, such as a wine or beer cellar. In such a room, the sensor is to be placed near the ground. Under German law, the sensor is to be placed 30 cm from the floor. Some manufacturers recommend placement 1 m from the floor. It is normally placed such that it is not damaged by activity in the room, such as damage by beer kegs in a beer cellar, where it might be placed 50 cm from the floor for this reason.

It is also known that during the kerosene combustion process, for example for heating, CO production starts at 9000 ppm $CO_2$ as combustion deteriorates at higher $CO_2$ concentrations.

SUMMARY OF THE PRESENT INVENTION

Technical Problems

Considering the prior art, such as it has been described above, there is a technical problem to provide a device for the detection and warning of $CO_2$ in harsh environments, such as environments with abundant water, grease or other substances that may affect the device.

There is a technical problem to provide a device for detection and warning of $CO_2$ that can easily be cleaned, without the device being thereby adversely affected.

There is a technical problem to provide a device for detection and warning of $CO_2$ which emits with simple means a strong audible signal in conjunction with a warning.

There is a technical problem to provide detection and warning of the presence of $CO_2$ in rooms continuously used as a working environment.

There is a technical problem to measure the presence of $CO_2$ in a room with ventilation, open windows or doors, and where people move in and through the room.

There is also a technical problem to simplify a device and thereby make it more economically affordable so that it can be practically useful for the public as a device or system for the detection of $CO_2$.

There is also a technical problem to provide an economically affordable device that is practically useful for the public as a device or system for the detection of CO.

The Solution

With the intention of solving one or more of the aforesaid technical problems, the present invention provides that a system for monitoring the $CO_2$ is placed in the immediate work environment, meaning adapted for e.g. the kitchen, meaning directly in the room where occupants work with $CO_2$ and adapted for the environment.

It is proposed that a device according to the present invention is an integrated unit in which both the gas-detecting unit with gas cell for detection of $CO_2$ and the alarming unit are integrated in one device. The alarming unit may comprise a light-emitting means for generating a flashing light and an audible means for generating an audible signal.

A device according to the present invention has an exterior casing which faces the room and is sealed to withstand fluid exposure in conjunction with cleaning or liquids present in the environment, as well as grease or oil. In order to allow for gas exchange into the gas cell active inside the unit, a portion of the casing which faces the unit's base opens for gas exchange but closes by means of interacting diagonal wall portions to prevent liquid from entering the unit.

According to one proposed embodiment of the present invention, these interacting wall portions are truncated cones of different sizes which face one another to form a system of wall portions through which no fluid can pass, while forming a sound amplification system of cones that produces a megaphone-like effect for the audible signal, and whereby gas flows easily for gas exchange in the gas cell.

A system of interacting truncated cones may, for example, comprise one first cone with its smaller opening facing in towards the device, the gas cell and the audible means; and its larger opening facing the base of the unit and a second cone, the second cone being larger than the first cone. This second cone may be open at its larger opening, which faces the first cone, and closed at its smaller opening, which faces the base of the unit. This closed portion creates a seal towards the base and a surface for a fastener for the unit. A third cone which is larger than the first and second cones is located above the first cone, with its larger opening facing, like the first cone, towards the second truncated cone. The smaller part of the third cone is closed by means of sealing between the third cone and the first cone.

The three cones overlap one another somewhat on the outer edge on the large end of the three cones, so that together they form inclined wall portions which prevent the possibility of liquid entering the gas cell, allow for gas exchange in the gas cell, and form the sound amplification system for the audible signal.

The first and third cones are integrated in the sealed casing of the device, while the other cone forms part of the attachment of the device to a base.

A first fastener is adapted to provide a fixed but removable attachment between the second cone and the sealed casing. The first fastener may comprise for example a screw joint in which the second cone is allocated a number of lug holes through which screws can be screwed and connect to threaded bores in the sealing casing. These threaded bores can, for example, be located on the first cone, the third cone, or on the sealing between the first and third cones.

The second cone can be allocated a second fastener adapted for interaction with a fastening plate, wherein the fastening plate is adapted to be secured to the base, and wherein the second fastener is adapted to a fixed but easily removable interaction between the second cone and the fastening plate. The second fastener may consist, for example, of a bayonet mount.

It is proposed that at least one portion of the casing which faces away from the base be transparent in order to let the flashing light through inside the casing; and that the transparent portion be of a colour which gives the warning light a colour appropriate for a warning signal.

In this way, both an audible signal and a light signal can be easily generated by the device according to the present invention.

This device can be adapted to issue various levels of alarm which can be determined by local legislation, for example, or ACGIH recommendations, which are accepted in the majority of countries in the world.

For example, a first level may be of the order of 5000 ppm Time Weighted Average (TWA) and a second level of the order of 1 to 3% STEL, where the first level warns of danger after prolonged exposure, but where the first level may be harmless in the event of short-term exposure; and where the second level warns of danger even in the event of short-term exposure. There might be, of course, only one or more than two levels of alarm.

An example of an additional alarm level is a third level that may be relevant in rooms where some form of kerosene combustion takes place, for example for heating or cooking. The present invention provides a third level set at 9000 ppm $CO_2$, since kerosene combustion deteriorates at higher concentrations of $CO_2$, resulting in CO accumulation. This third level is thus intended as a warning of CO accumulation.

An alarm system according to the present invention is a leak alarm, unlike life-saving alarms of the prior art, whereby the leak alarm warns of a change in the room environment. Such a room can be a working or living environment where there is a need to monitor dangerous levels of $CO_2$ and/or CO. The present invention can be adapted for use in various industrial premises and in workplaces such as restaurant kitchens, and also for private use, such as in homes, holiday homes, caravans and boats.

The invention thus provides that the sensor and warning indicator must be integrated in one unit, unlike the prior art where the sensor is located in one room while the alarming unit is located in another room. The device according to the present invention is to be placed and is to operate in an environment meeting statutory requirements for ventilation where air movement is created by human motion. It is therefore proposed that the device be installed at head height of the occupants of the room, and it is possible for a plurality of devices to be connected and installed in the same room.

It is proposed that a warning at the first alarm level could consist of the integrated flashing light, and that the warning at the second alarm level could consist of an audible signal from the integrated siren, which can also emit a unique clicking sound that would be less disruptive to surrounding rooms than the siren.

Prior art systems for $CO_2$ measurement are large, and if they are to be integrated into a device and installed according to the present invention, they would be very large and bulky. In order to provide an integrated unit that can easily be installed at head height in a working environment without being bulky, a $CO_2$ detector adapted to be of sufficiently small size for such an integration is required. It is proposed that a gas sensor be used that is adapted for $CO_2$ detection through absorption of infrared light, a so-called infrared sensor. A possible sensor unit which is sufficiently small to be used with the present invention is described and illustrated in the Swedish patent application SE 0901378-0, entitled "A Measuring Cell Adapted to Spectral Analysis" by the applicant SenseAir AB.

The device according to the present invention can be adapted for fixed installation, preferably against a wall.

The device according to the present invention includes components which are normally operated at 12 to 24 volts. Such an operating voltage can be obtained by connecting the device to the public grid and by the device also comprising an integrated transformer which supplies the necessary voltage. It is also possible to use an external transformer connected to the public grid that supplies the required voltage to the device. No matter which voltage supply method is chosen, it is proposed that the connection to the public grid be secured with some type of lock, such as a "plug-lock" so that the operating voltage to the device is not disconnected accidentally. It is also possible to use internal battery operation, such as a so-called ultracapacitor, in the device. It is also possible to operate a device according to the present invention, or charge the ultracapacitor for a device according to the present invention, with light cells.

A method according to the present invention consists of measuring $CO_2$ in the room in which persons/people are working and of the alarming unit being placed in this room to directly issue the alarm to the occupants of the room.

It is also possible to provide a first interface for communication, wherein an external alarm signal can be issued to the areas outside the monitored room. It is also possible to provide a second interface for communication, an interface for digital communications, whereby it is possible to communicate with the device for service purposes and if one wishes to keep a log of the measured gas concentrations. Both the first and the second interfaces for communication may consist of a wired or a wireless interface. There is nothing to prevent the first and second interfaces from consisting of a shared interface, such that only the second interface exists, but that it is also adapted for communication of an external alarm signal. The device according to the present invention can thus be included in a system of a plurality of devices where various rooms can be monitored from a central position from which it is possible to communicate with devices comprised by the system.

Advantages

The advantages that foremost may be regarded as characteristic of a method and device according to the present invention is that in this way, the $CO_2$ concentration can be measured continuously in a room/working environment occupied by people working or living, and this with one or more small, simple integrated devices that comprise both a gas-measuring unit and an alarming unit. The device is simple to manufacture, can be manufactured in a cost effective manner and can also easily be installed in rooms where it is important to monitor the $CO_2$ concentration to thereby monitor the working or living environment of the room. There is also a possibility to monitor dangerous levels of CO in rooms where incomplete combustion of kerosene, for example, takes place with small devices adapted to both industrial use and private use such as in homes, holiday homes, caravans and boats.

FIGURE DESCRIPTION

Figure 3:
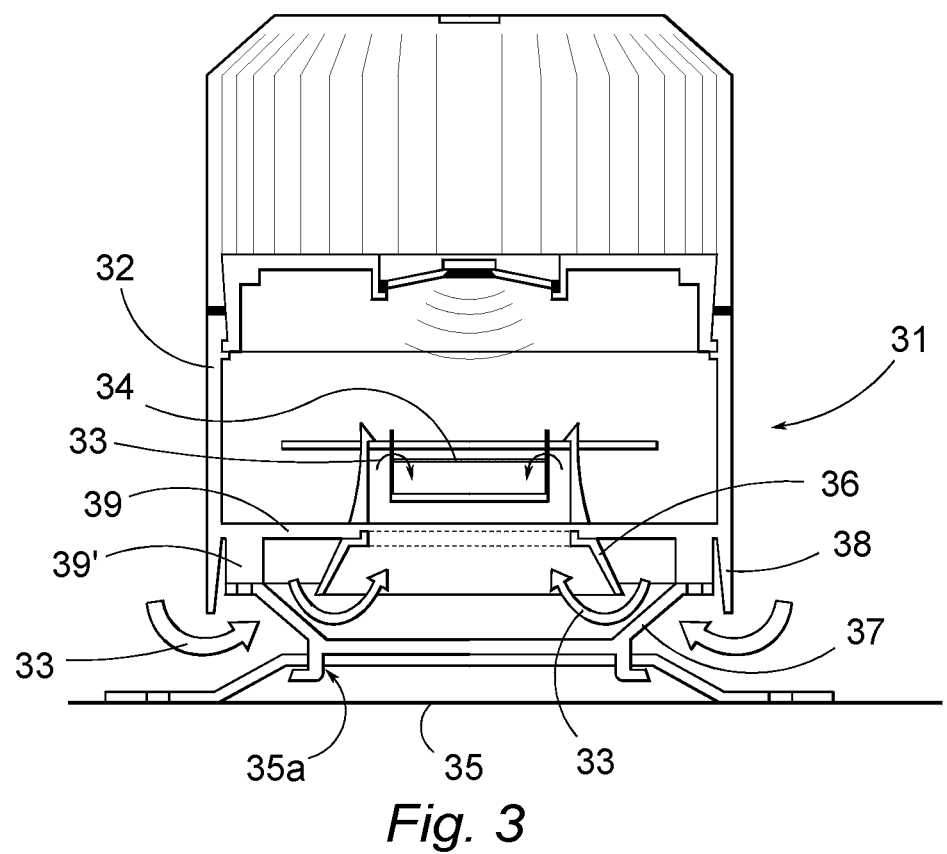
Figure 4:
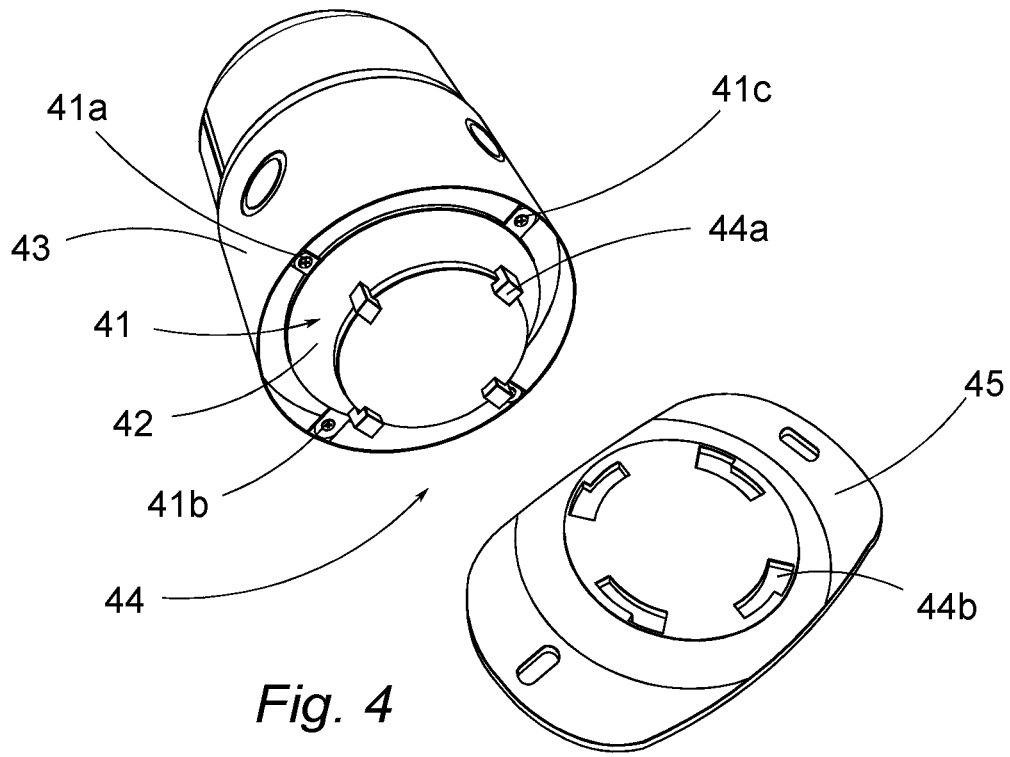
Figure 5:
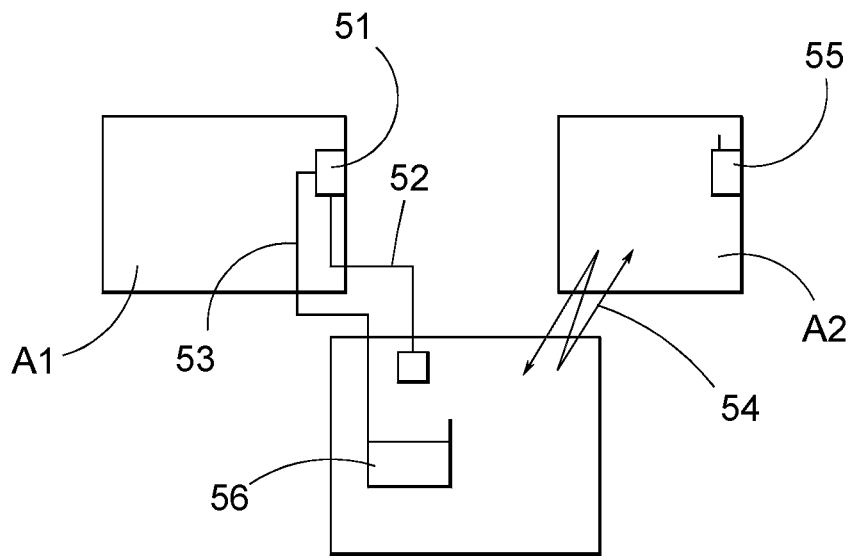

A device and method having characteristics associated with the present invention are shown schematically in the accompanying drawing in which:

FIG. 1 schematically and in a greatly simplified manner shows an alarm system for $CO_2$ according to the prior art, FIG. 2 schematically and in a greatly simplified manner shows a device according to the present invention, FIG. 3 shows a cross section of a device according to the present invention;

FIG. 4 shows a perspective representation of the device according to the present invention, and FIG. 5 shows schematically and in a greatly simplified manner a system of interacting devices.

DETAILED DESCRIPTION OF PREFERRED EMBODIMENTS

With reference being made to the figures, a device according to the present invention will now be described.

FIG. 1 shows schematically and in a greatly simplified manner an alarm system for $CO_2$ according to the prior art whereby the sensor 11 is located inside a room A and the alarm unit 12 is located outside the room A to warn of the danger of entering the room A due to the presence of $CO_2$ in the room A.

FIG. 2 shows schematically and in a greatly simplified manner a device 21 according to the present invention comprising a gas-detecting unit 22 for the detection of $CO_2$ and an alarming device 23 integrated into device 21. The device 21 is located in room A' and thus can measure the environment in room A' and warn the persons 24 who are occupying and working or living in room A'.

FIG. 3 shows a cross section of the exterior casing 32 which faces the room and belongs to device 31. Casing 32 is sealed to withstand exposure to liquids. In order to allow an exchange of gas 33 to the gas cell 34 active within the unit, a portion of the casing 32 which faces the base 35 of the device is open for gas exchange, but closed by means of interacting inclined wall portions 36, 37 and 38 which prevent liquid from entering the unit.

These interacting wall sections may consist of truncated cones of different sizes which face one another to form a system of wall portions through which no fluid can pass, while forming a sound amplification system of cones that produces a megaphone-like effect for the audible signal, and whereby gas flows easily for gas exchange in the gas cell.

In the embodiment according to figure there are a first 36, a second 37 and a third 38 interacting cones.

FIG. 4 shows schematically a first fastener 41 adapted to provide a fixed but removable attachment between the second cone 42 and the sealed casing 43. This first fastener 41 consists in the exemplary figure of a screw joint whereby the second cone 42 is allocated a number of lug holes 41a, 41b, 41c through which screws can be screwed and connected to threaded bores in the sealing casing 43. These threaded bores can, for example, be located on the first cone, the third cone, or, as is shown more clearly in FIG. 3, such that the threaded bore is located in a mount 39' which in turn is located in the seal 39 between the first and third cones 36, 38.

FIG. 4 also shows that the second cone 42 may be allocated a second fastener 44 adapted for interaction with a fastening plate 45, where the fastening plate is adapted to be attached to the base. The second fastener 44 is adapted for a firm but easily removable interaction between the second cone 42 and fastening plate 45. The second fastener may, for example, as is shown in the figure, comprise a bayonet mount with a first bayonet section 44a and a second bayonet section 44b adapted for interaction, whereby an interacting fastener 35a is shown in FIG. 3.

FIG. 5 shows that a device 51 according to the present invention can be adapted to communicate using a first communication interface 52 and/or a second communication interface 53, whereby the first interface 52 is adapted to transmit an external alarm signal to the area A2 outside of the monitored room A1.

The second interface for communication 53, an interface for digital communication, through which it is possible to communicate with the device 51 for service purposes and, if one wishes, to keep a log of the measured gas concentrations.

Both the first and the second interface 52, 53 for communication may comprise a wired interface or a wireless interface 54. There is nothing to prevent the first and second interfaces from consisting of a shared interface, such that only the second interface exists, but that it is also adapted for communication of an external alarm signal.

The device according to the present invention can thus be included in a system of a plurality of devices 51, 55 in which different rooms A1, A2 can be monitored from a central position 56 from which it is possible to communicate with the devices 51, 55 comprised by the system.

The invention is of course not limited to the above exemplary embodiments, but may undergo modifications within the scope of the concept according to the present invention as defined by the following claims.

The invention claimed is:

1. A device for detection of $CO_2$, comprising:
    an integrated unit including a gas-detecting device having a gas cell for detection of $CO_2$, an alarming unit, and an exterior casing facing a room in which the device is located;
    wherein said casing is sealed to withstand exposure to fluids and grease or oil and a part of said casing which faces a base of the device is open for gas exchange in order to allow for an exchange of gas to said gas cell, but is closed for the entry of liquids by a plurality of interacting inclined wall portions.

2. The device according to claim 1, wherein said alarming unit comprises a light-emitting means for generating a flashing light and an audible means for generating an audible signal.

3. The device according to claim 2, wherein said interacting inclined wall portions are truncated cones of different sizes which face one another to form a system of wall portions through which no fluid can pass while forming a sound amplification system of truncated cones that produces a megaphone-like effect for the audible signal, and whereby gas flows easily for gas exchange in the gas cell.

4. The device according to claim 3, wherein said system of interacting truncated cones comprises:
    a first cone with a smaller opening facing towards the gas cell and the audible means, and a larger opening facing the base of said device and facing a second cone;
    said second cone being larger than said first cone, said second cone having a larger opening facing said first cone and being closed at a smaller closed end which faces said base of said device; said closed end comprising a seal against said base and a surface for fastening of said unit to said base; and
    a third cone which is larger than said first cone and said second cone and is positioned above said first cone, wherein a larger opening of said third cone faces said second cone, and wherein a smaller portion of said third cone is closed by a seal between said third cone and said first cone.

5. The device according to claim 4, wherein said three cones overlap one another somewhat on the outer edges of the larger openings of the three cones to form said inclined wall portions.

6. The device according to claim 4, wherein said first and said third cones are integrated in said casing, and that said second cone attaches said unit to said base.

7. The device according to claim 6, wherein a first fastener is adapted to provide a fixed but removable attachment between said second cone and said casing.

8. The device according to claim 7, wherein said first fastener comprises a plurality of screw joints, and said second cone includes a plurality of lug holes through which screw joints can be screwed and connect to a plurality of threaded bores in said casing.

9. The device according to claim 8, wherein said threaded bores are located in said first cone.

10. The device according to claim 8, wherein said threaded bores are located in said third cone.

11. The device according to claim 8, wherein said threaded bores are located in the seal between said first and third cones.

12. The device according to claim 6, wherein said second cone includes a second fastener adapted for interaction with a fastening plate, said fastening plate being adapted to be secured to said base, and said second fastener being adapted to a fixed but easily removable interaction between said second cone and said fastening plate.

13. The device according to claim 12, wherein said second fastener comprises a bayonet mount.

14. The device according to claim 2, wherein at least one portion of the casing faces away from said base and is transparent in order to let the flashing light through the casing; and
wherein said transparent portion be of a color which gives the flashing light a color appropriate for a warning signal.

15. The device according to claim 1, wherein said device is adapted to issue alarms of different levels.

16. The device according to claim 15, wherein a first level warns of the danger of prolonged exposure, the first level being harmless in the event of short-term exposure, and wherein a second level warns of danger in the event of short-term exposure.

17. The device according to claim 16, wherein said first level is of the order of 5000 ppm $CO_2$ Time Weighted Average and said second level is of the order of 1 to 3% Short Time Exposure Limit.

18. The device according to claim 17, wherein a third level is set at 9000 ppm $CO_2$.

19. The device according to claim 16, wherein a warning at the first level consists of a flashing light, and a warning at said second level consists of an audible signal.

20. The device according to claim 19, in that wherein said audible signal comes from said integrated a siren.

21. The device according to claim 19, wherein said audible signal comprises a clicking sound.

22. The device according to claim 1, wherein said gas cell is a gas sensor adapted for the detection of $CO_2$ by absorbing infrared light.

23. The device according to claim 1, wherein said device is adapted for fixed installation.

24. The device according to claim 1, further comprising:
an integrated transformer which is adapted to supply a required voltage when said device is connected to a public grid.

25. The device according to claim 1, wherein said device is connected to an external transformer which supplies a required voltage to said device, said external transformer being connected to a public grid.

26. The device according to claim 24, wherein the connection to the public grid is secured with a lock.

27. The device according to claim 1, further comprising:
an internal battery which is adapted to supply a required voltage.

28. The device according to claim 27, wherein said internal battery is an ultracapacitor.

29. The device according to claim 1, further comprising:
a plurality of light cells adapted to supply a required voltage.

30. The device according to claim 28, further comprising:
a plurality of light cells that are adapted to charge said ultracapacitor.

31. The device according to claim 1, further comprising:
a first interface for communication, whereby an external alarm signal can be issued to areas outside the room.

32. The device according to claim 31, further comprising:
a second interface for communication, said second interface being an interface for digital communication, whereby it is possible to communicate with the device for service purposes and to keep a log of measured gas concentrations.

33. The device according to claim 32, wherein both said first and said second interfaces for communication are comprised of a wired interface.

34. The device according to claim 32, wherein both said first and said second interfaces for communication are comprised of a wireless interface.

35. The device according to claim 33, wherein said first and second interfaces are comprised of a shared interface.

36. The device according to claim 1, further comprising:
a second interface for communication, said second interface being an interface for digital communication, wherein said second interface is adapted for communication of an external alarm signal.

37. A system comprising:
a plurality of interacting devices for detection of $CO_2$, wherein each of the devices comprises:
an integrated unit including a gas-detecting device having a gas cell for detection of $CO_2$ an alarming unit, and an exterior casing facing a room in which the device is located;
wherein said casing is sealed to withstand exposure to fluids and grease or oil;
wherein a part of said casing which faces a base of the device is open for gas exchange in order to allow for an exchange of gas to said gas cell, but is closed for the entry of liquids by a plurality of interacting inclined wall portions.

38. The system according to claim 37, wherein the plurality of interacting devices are monitored from a central position from which it is possible to communicate with the plurality of interacting devices.

* * * * *